United States Patent
Muller et al.

(10) Patent No.: US 9,304,051 B2
(45) Date of Patent: Apr. 5, 2016

(54) SMART SENSOR UNIT WITH MEMORY METAL ANTENNA

(71) Applicant: enLighted, Inc., Sunnyvale, CA (US)

(72) Inventors: Peter H. Muller, Woodside, CA (US); Michel Billard, Sunnyvale, CA (US); Tanuj Mohan, Mountain View, CA (US)

(73) Assignee: enLighted, Inc., Sunnyvale, CA (US)

( * ) Notice: Subject to any disclaimer, the term of this patent is extended or adjusted under 35 U.S.C. 154(b) by 0 days.

(21) Appl. No.: 14/596,496

(22) Filed: Jan. 14, 2015

(65) Prior Publication Data

US 2015/0127260 A1  May 7, 2015

Related U.S. Application Data

(63) Continuation-in-part of application No. 13/930,009, filed on Jun. 28, 2013, now abandoned, which is a continuation of application No. 12/849,081, filed on Aug. 3, 2010, now Pat. No. 8,508,149.

(60) Provisional application No. 61/934,008, filed on Jan. 31, 2014.

(51) Int. Cl.
| | |
|---|---|
| *G01K 13/00* | (2006.01) |
| *G01N 25/56* | (2006.01) |
| *G01J 1/00* | (2006.01) |
| *H05B 37/02* | (2006.01) |
| *H04W 84/18* | (2009.01) |

(52) U.S. Cl.
CPC . *G01K 13/00* (2013.01); *G01J 1/00* (2013.01); *G01N 25/56* (2013.01); *H05B 37/0272* (2013.01); *H04W 84/18* (2013.01); *Y02B 20/48* (2013.01); *Y10T 29/49716* (2015.01)

(58) Field of Classification Search
None
See application file for complete search history.

(56) References Cited

U.S. PATENT DOCUMENTS

| | | | |
|---|---|---|---|
| 5,101,141 A | 3/1992 | Warner et al. | |
| 5,179,324 A | 1/1993 | Audbert | |
| 5,191,265 A | 3/1993 | D'Aleo et al. | |
| 5,283,516 A | 2/1994 | Lohoff | |
| 5,385,297 A * | 1/1995 | Rein et al. | 236/49.3 |
| 5,553,006 A * | 9/1996 | Benda | 700/276 |
| 5,812,422 A | 9/1998 | Lyons | |
| 5,970,393 A * | 10/1999 | Khorrami | H01Q 3/46 340/10.34 |
| 6,057,654 A | 5/2000 | Cousy et al. | |
| 6,188,181 B1 | 2/2001 | Sinha et al. | |
| 6,342,994 B1 | 1/2002 | Cousy et al. | |
| 6,548,967 B1 * | 4/2003 | Dowling et al. | 315/318 |
| 7,309,985 B2 | 12/2007 | Eggers et al. | |
| 7,348,736 B2 * | 3/2008 | Piepgras et al. | 315/291 |
| 7,382,271 B2 * | 6/2008 | McFarland | 340/686.6 |

(Continued)

*Primary Examiner* — Crystal L Hammond
(74) *Attorney, Agent, or Firm* — Brian R. Short (57) ABSTRACT

Systems, method and apparatuses of a building control sensor unit are disclosed. One apparatus includes a building control sensor unit that includes one or more sensors operative to sense an environmental condition of a structure, and a transceiver, wherein the transceiver includes an extended antenna, wherein the extended antenna includes a strand of memory metal. The apparatus further includes a controller, wherein the controller is operative to receive information from other building control sensor units or a central controller, and transmit information to the other building control sensor units or the central controller, wherein the building control sensor unit is configured such that when placed on or within a ceiling of the structure, the extended antenna extends into the structure.

20 Claims, 5 Drawing Sheets

(56) References Cited

U.S. PATENT DOCUMENTS

| | | | |
|---|---|---|---|
| 7,437,596 B2 * | 10/2008 | McFarland | 714/47.2 |
| 7,550,931 B2 * | 6/2009 | Lys et al. | 315/291 |
| 7,566,137 B2 | 7/2009 | Veskovic | |
| 7,623,042 B2 | 11/2009 | Huizenga | |
| 7,792,956 B2 | 9/2010 | Choong et al. | |
| 7,812,543 B2 | 10/2010 | Budike, Jr. | |
| 7,925,384 B2 | 4/2011 | Huizenga et al. | |
| 2004/0002792 A1 | 1/2004 | Hoffknecht | |
| 2005/0169643 A1 * | 8/2005 | Franklin | H04B 10/1141 398/187 |
| 2005/0280598 A1 * | 12/2005 | Webb | H01Q 1/22 343/718 |
| 2006/0028997 A1 * | 2/2006 | McFarland | 370/252 |
| 2006/0273970 A1 * | 12/2006 | Mosebrook | H01Q 1/22 343/718 |
| 2006/0275040 A1 | 12/2006 | Franklin | |
| 2007/0057807 A1 | 3/2007 | Walters et al. | |
| 2007/0061050 A1 | 3/2007 | Hoffknecht | |
| 2007/0086128 A1 | 4/2007 | Lane et al. | |
| 2007/0215794 A1 | 9/2007 | Cernasov et al. | |
| 2008/0185977 A1 | 8/2008 | Veskovic et al. | |
| 2008/0244104 A1 | 10/2008 | Clemente | |
| 2008/0265796 A1 | 10/2008 | Null | |
| 2009/0026966 A1 | 1/2009 | Budde et al. | |
| 2009/0140059 A1 * | 6/2009 | Barton et al. | 236/51 |
| 2009/0179596 A1 | 7/2009 | Willaert et al. | |
| 2009/0195161 A1 | 8/2009 | Lane et al. | |
| 2010/0034386 A1 | 2/2010 | Choong et al. | |
| 2010/0135186 A1 | 6/2010 | Choong et al. | |
| 2010/0150060 A1 * | 6/2010 | Vitek | G01C 9/00 370/328 |
| 2010/0264846 A1 | 10/2010 | Chemal et al. | |
| 2010/0270933 A1 | 10/2010 | Chemal et al. | |
| 2010/0280677 A1 | 11/2010 | Budike, Jr. | |
| 2010/0295482 A1 | 11/2010 | Chemal et al. | |
| 2010/0301777 A1 | 12/2010 | Kraemer | |
| 2011/0031897 A1 | 2/2011 | Henig et al. | |
| 2011/0199020 A1 | 8/2011 | Henig et al. | |
| 2011/0210843 A1 * | 9/2011 | Kummetz | G01S 5/0289 340/517 |
| 2013/0285544 A1 * | 10/2013 | Molezion | H01Q 1/007 315/34 |

\* cited by examiner

SMART SENSOR UNIT WITH MEMORY METAL ANTENNA

RELATED APPLICATIONS

This patent application is a CIP (continuation-in-part) of U.S. patent application Ser. No. 13/930,009, filed Jun. 28, 2103, which is a continuation of U.S. patent application Ser. No. 12/849,081, filed Aug. 3, 2010, and granted as U.S. Pat. No. 8,508,149, which are incorporated by reference. Further, this patent application claims priority to U.S. Provisional Patent Application Ser. No. 61/934,008, filed Jan. 31, 2014, which is incorporated by reference.

FIELD OF THE EMBODIMENTS

The described embodiments relate generally to building environmental control. More particularly, the described embodiments include a smart sensor system that includes a memory metal antenna, wherein the smart sensor system provides environmental control of a structure.

BACKGROUND

Lighting control systems automate the operation of lighting within a building or residence based upon, for example, preset time schedules and/or occupancy and/or daylight sensing. The Lighting systems typically employ occupancy sensors and/or daylight sensors to determine which lighting devices to activate, deactivate, or adjust the light level of, and when to do so. Occupancy sensors typically sense the presence of one or more persons within a defined area and generate signals indicative of that presence. Daylight sensors typically sense the amount of daylight present within a defined area and generate signals indicative of that amount. Typically, lighting systems receive the sensor signals at a central lighting controller.

The lighting systems are advantageous because they typically reduce energy costs by automatically lowering light levels or turning off devices and appliances when not needed, and they can allow all devices in the system to be controlled from one location.

It is desirable to have a method, system and apparatus for smart sensor system of environmental control of a structure.

SUMMARY

One embodiment includes a building control sensor unit. The building control sensor unit includes one or more sensors operative to sense an environmental condition of a structure, a transceiver, wherein the transceiver includes an extended antenna, wherein the extended antenna includes a strand of memory metal. The building control sensor unit further includes a controller, wherein the controller is operative to receive information from other building control sensor units or a central controller, and transmit information to the other building control sensor units or the central controller. The building control sensor unit is configured whereby when placed on or within a ceiling of the structure, the extended antenna extends into the structure.

Another embodiment includes a building control system. The building control system includes a plurality of building control sensor units, wherein at least one of the plurality of building control sensor units communicates with at least one of another one of the plurality of building control sensor units or a central control unit. At least one of the plurality of building control sensor units includes one or more sensors operative to sense an environmental condition of a structure. The building control sensor unit further includes a transceiver, wherein the transceiver includes an extended antenna, wherein the extended antenna includes a strand of memory metal, a controller, wherein the controller is operative to receive information from other building control sensor units or the central controller, and transmit information to the other building control sensor units or the central controller, wherein the at least one of the plurality of building control sensor units is configured whereby when placed on or within a ceiling of the structure, the extended antenna extends into the structure.

Other aspects and advantages of the described embodiments will become apparent from the following detailed description, taken in conjunction with the accompanying drawings, illustrating by way of example the principles of the described embodiments.

DETAILED DESCRIPTION

As shown in the drawings, the described embodiments are embodied in an apparatuses, methods, and systems for a smart sensor apparatus, method and system for aiding environmental control of a structure, according to an embodiment. An embodiment includes an extendable antenna that includes a memory metal antenna.

Figure 1:
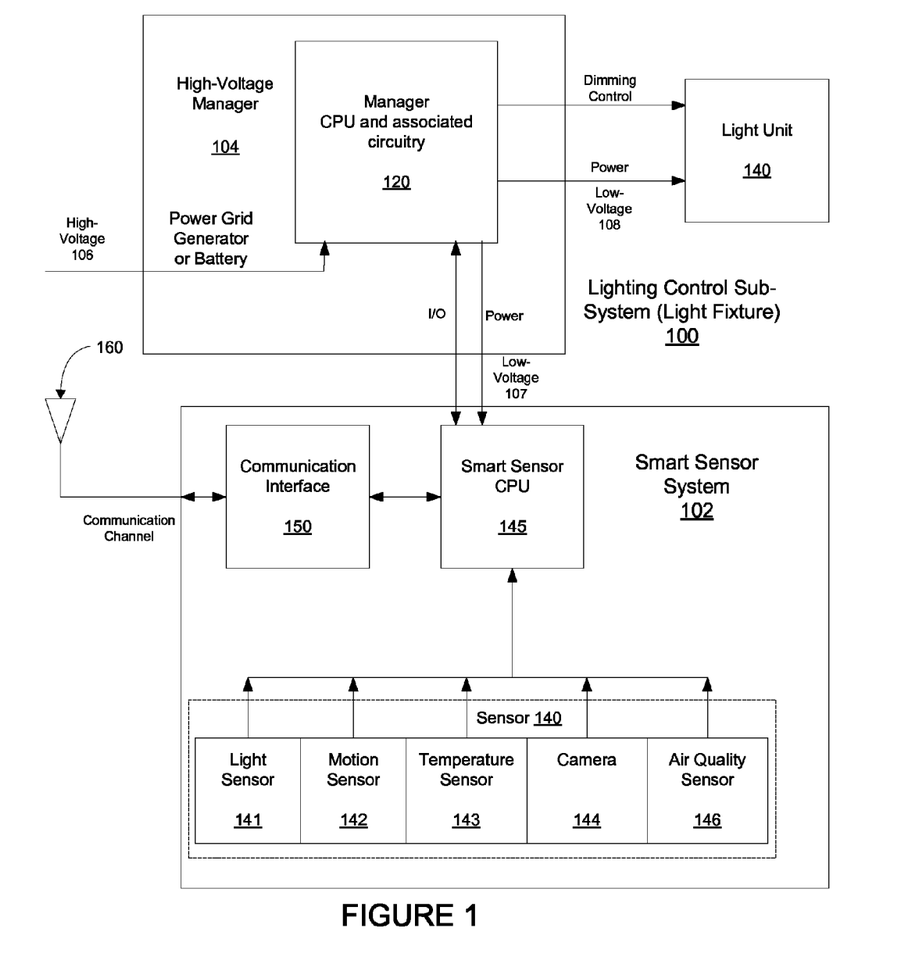
FIG. 1 shows an independently controllable light fixture, according to an embodiment.

FIG. 1 shows an embodiment of a light fixture 100 that can be utilized as the fixture of the described embodiments. This embodiment of the light fixture 100 includes a high-voltage manager 104 and a smart sensor system 102 that include a manager CPU 120 and smart sensor CPU 145 that operate in conjunction as a controller that independently manages and controls the operation of the light fixture 100. An embodiment of the smart sensor system 102 includes the building control sensor unit with a memory metal antenna as will be described. The light fixture 100 can include any combination of sensors (140), such as, a light sensor 141, a motion sensor 142, a temperature sensor 143, a camera 144, and/or an air quality sensor 146. The light fixture 100 can receive profiles from elsewhere over a communications channel.

For the embodiment of FIG. 1, the high-voltage manager 104 receives a high voltage (for example, 120 Volts) 106 and generates a power supply voltage for both the smart sensor system 102 (for example, 5 Volts) and the lighting unit 140, and a dimming control for the lighting unit 140. For an embodiment, the low power 107 and/or the low power 108 provided by the high-voltage manager 104 is a stepped down voltage from the high voltage 106 received by the high-voltage manager 104. That is, the typically 120 volts of the high voltage 106 is stepped down within the high-voltage manager 104 to the low voltages (for example, 5 volts) of the low power voltages 107, 108. Owing to the power supply voltage of the smart sensor system 102 being the low voltage, the smart sensor system 102 can more easily and less expensively be installed because a lower-level, less costly technician can be used to install the smart sensor system 102.

For this embodiment, both the high-voltage manager 104 and the smart sensor system 102 include CPUs (central processing units) 120 and 145 which operate in conjunction to control the lighting unit 140. While shown as separate controllers, it is to be understood that the operations and functionality of the two CPUs could be included within a single controller.

As shown, the light fixture 100 includes the light unit 140. It is to be understood that the light unit 140 could alternatively be external to the fixture. For this embodiment, the controller (manager CPU 120 and smart sensor CPU 145) can include outputs to effect the light level changes. For example, the outputs can control relays to turn lights on and off, and control 0-10 V or PWM (pulse width modulation) outputs for dimming. The light unit 140 can include one or more light emitting diodes (LEDs), and the dimming control can be provided by controlling a current supplied to the one or more LEDs. The controller 120 can include a standard chipset that integrates a microprocessor unit, and interface for communicating different program instructions, and several ports for communicating with electronic devices.

The light fixture 100 additionally includes an interface 150 that allows the lighting fixture to communicate with the central controller through the communications link. The interface 150 can be a wired (for example Ethernet®), or the interface can be wireless (for example, Zigbee®). The interface 150 can provide a direct link to the central controller, or the interface can provide an intermediate link to an intermediate device (such as the previously described gateway). As shown, for an embodiment, the communication interface is included within the smart sensor system 102 rather than within the high-voltage manager 104. Communication to or from the high-voltage manager through the communication interface 150 is facilitated by the smart sensor CPU 145.

For a wireless interface, the communications link is established through an antenna 160. As will be described, for an embodiment, the antenna is fabricated out of a memory metal. Further, the antenna 160 extends out of a metal casing or fixture of the smart sensor system 102. Further, for an embodiment, when the smart sensor system 102 and the lighting control sub-system 100 are affixed to a wall or ceiling of a structure, the antenna fabricated from a memory metal extends into the structure.

While the lighting fixture 100 provides lighting control, it is to be understood the equivalent fixtures for controlling other environmental parameters, such as, temperature, and humidity can additionally or alternatively be implemented according to the described embodiments. Accordingly, the control information can include at least one of light intensity, lighting scenes, thermostat, and/or a security alarm.

For embodiments, the communication link comprises at least one of a cellular link to a service provider wherein the central controller is connected to the service provider, or an 802.11 wireless link between the user device and the central controller.

Further, other channels of communication between the smart sensor CPU 145 (of the lighting fixture 100) can be established through any of the sensors 141, 142, 143, 144, 146. For example, and light modulation communications link can be established through the light sensor 141, or an acoustic communication link can be established through the motion sensor 142.

For an embodiment, the high-voltage manager 104 provides low-power voltage to a plurality of smart sensor systems (building control sensor units). That is, for an embodiment, the high-voltage manager receives a high-voltage power and steps down the high-voltage power to a low-voltage power, and provides the low-voltage power to each of the plurality of building control sensor units. Further, for an embodiment, a processing unit (such as, CPU 120) of the high-voltage manager 104 communicates with an external controller through at least one of the plurality of building control sensor units. That is, for example, the CPU 120 of the high-voltage manager 104 communicates with the external controller through, for example, the smart sensor system (building control sensor unit) 102 through the smart sensor CPU 145, the communication interface 150 and the antenna 160.

Figure 2:
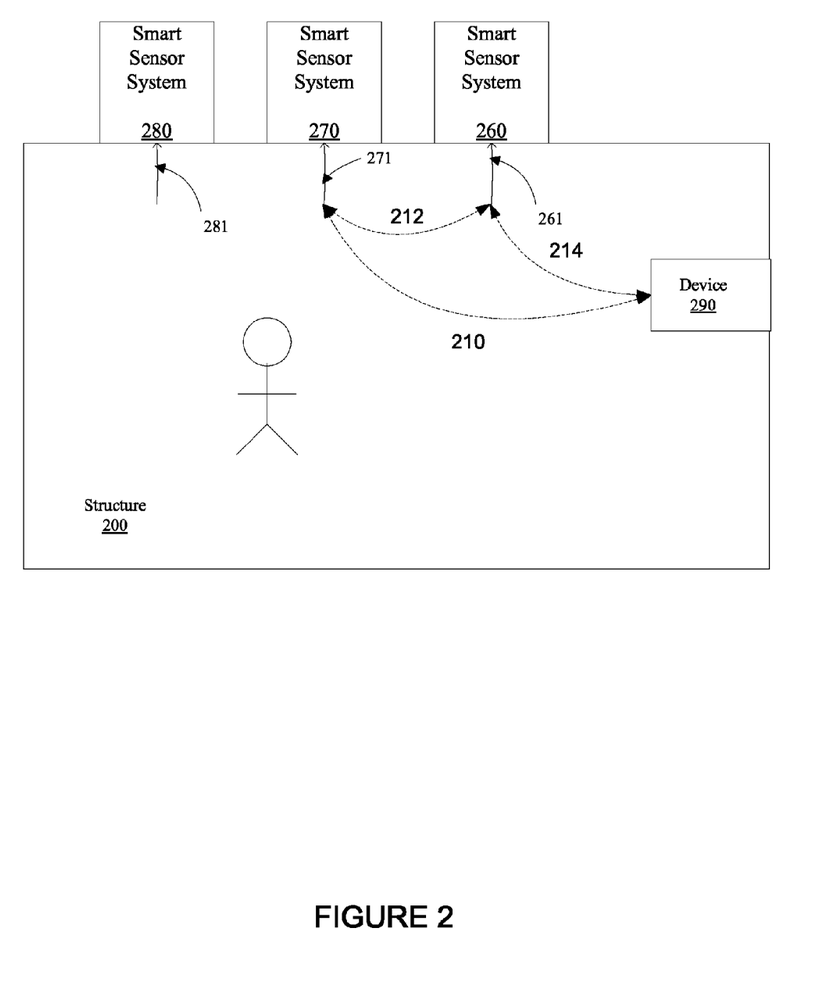
FIG. 2 shows a plurality of independently controlled light fixtures within a structure, according to an embodiment.

FIG. 2 shows a plurality of independently smart sensor systems 260, 270, 280 within a structure 100, according to an embodiment. As shown, each of the smart sensor systems 260, 270, 280 includes an antenna 261, 271, 281. As previously described, the antenna of at least one of the smart sensor systems 260, 270, 271 includes a memory metal, and the antenna extends into the room or structure in which the at least one of the smart sensor systems 260, 270, 271 is located. Due to the antennas 261, 271, 281 extending into the structure, wireless communication links between the at least one of the smart sensor systems 260, 270, 271 and another device is more likely to include a direct line of site (LOS). That is, obstructions to the wireless communication links are less likely to occur because the antennas 161, 171, 181 extend into the structure. The direct LOS path generally provides a higher-quality communications link that a non-direct LOS path. That is, if the smart sensor systems 260, 270, 280 were configured such that the antenna did not extend into the structure, the communications links formed by the corresponding antennas would not be as good.

As shown, a direct LOS communication link 210 is formed between, for example, the smart sensor system 270 and a device 290. Further, a direct LOS communication link 212 is formed between, for example, a first smart sensor system 270 and a second smart sensor system 260. Further, a direct LOS communications link 214 is formed between the second smart sensor system 260 and the device 290.

Figure 3:
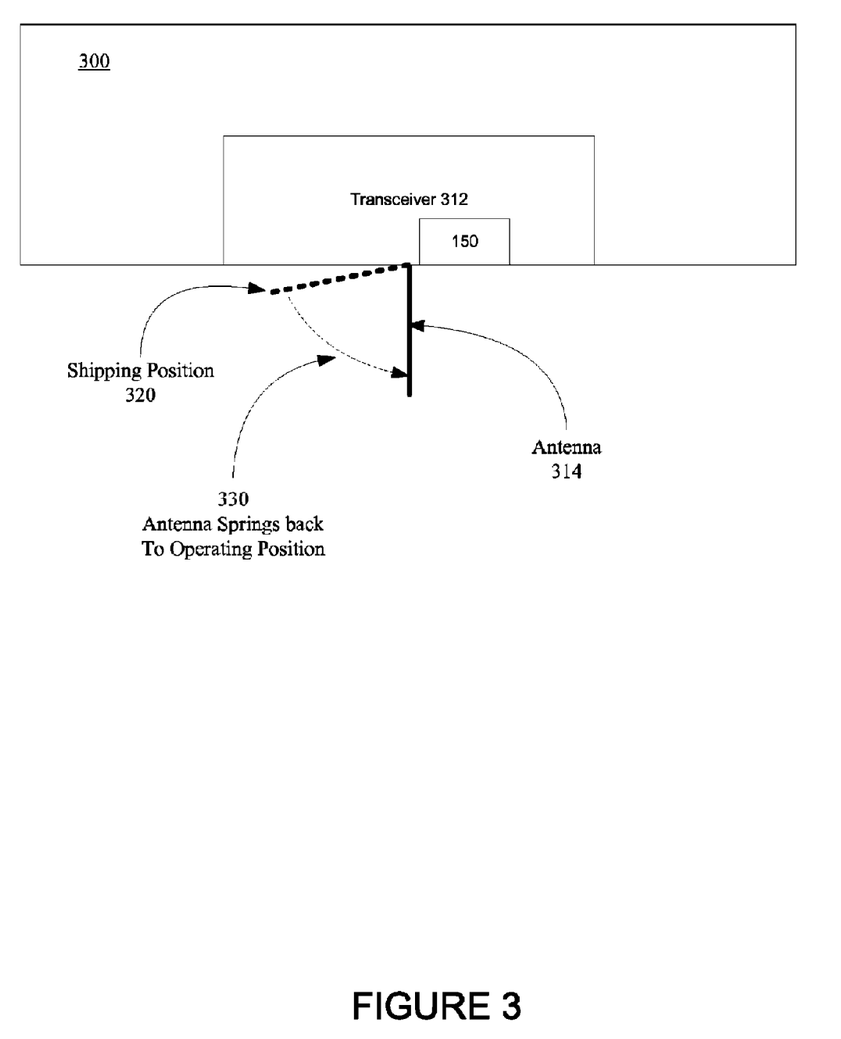
FIG. 3 shows an independently controllable light fixture, according to another embodiment.

FIG. 3 shows an independently controllable light fixture 300, according to another embodiment. A transceiver 312 includes at least the communication interface 150, and communicates with other devices through the antenna 314. For an embodiment, the transceiver 312 is included within a structure (such as, structure 200 of FIG. 2) of the independently controllable light fixture 300. However, when operating, the antenna 314 extends into a room or structure in which the independently controllable light fixture 300 is located.

For an embodiment, the antenna 314 extends through a ceiling of the room or structure. As previously described, for at least some embodiments, the antenna 314 is fabricated out of a memory metal that is able to maintain its extended shape characteristics even when temporarily deformed. For example, when the independently controllable light fixture 300 is placed in a box for shipping, the antenna 314 may be deformed to allow the independently controllable light fixture 300 to fit within a shipping box or container. When the independently controllable light fixture 300 is removed from the box or container after shipping, the antenna 314 extends back to its desired position relative to the rest of the independently controllable light fixture 300.

For an embodiment, the antenna 314 includes a single strand of memory metal. For another embodiment, the antenna 314 includes more than a single strand of memory metal, but retains the memory function of returning to its intended original shape after being deformed for some period of time.

As shown, during for example shipping of the light fixture 300, the antenna 314 is deformed to the position 320. However, upon removal from the shipping package, the memory metal of the antenna 314 causes the antenna to spring back (indicated by arrow 330) to its original or deployed operating position. Owing to the antenna 314 being manufactured out of the memory metal, the light fixture 300 is easier to package and ship, while still maintaining a configuration that is adapted to forming the desired LOS communication links when deployed.

Figure 4:
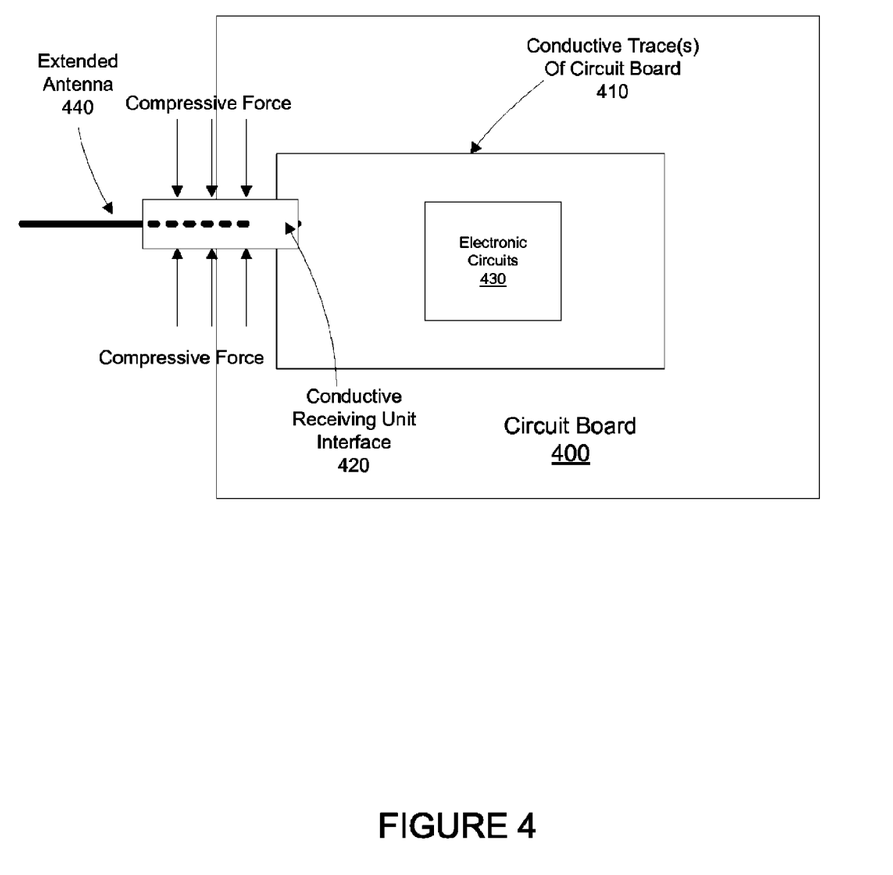
FIG. 4 shows a circuit board of a light fixture that includes a memory metal antenna electrically connected to the circuit board, according to an embodiment.

FIG. 4 shows a circuit board 400 of a building control sensor unit that includes a memory metal antenna 440 electrically connected to the circuit board 400, according to an embodiment. At least some embodiments of the memory metal antenna are formed from materials that cannot be easily soldered to. That is, the memory metal antenna does not "wet" when solder is placed in contact with a heated memory metal antenna. Due to the fact that these memory metal antennas can be very difficult to solder to, placing them in electrical contact with electrical components on the circuit board 400 can be difficult.

An embodiment includes electrically connecting the memory metal antenna 440 to the circuit board through a conductive receiving unit interface 420. The memory metal antenna 440 is inserted into the conductive receiving unit interface 420, and electrical contact between the memory metal antenna 440 and the conductive receiving unit interface 420 is realized by compressing the conductive receiving unit interface 420 around the memory metal antenna 420.

The conductive receiving unit interface 420 can be realized using many different shapes, as long as electrical and mechanical contact of the memory metal antenna 440 is realized when the conductive receiving unit interface 420 is compressed around or onto the memory metal antenna 440. For example, for an embodiment, the conductive receiving unit interface 420 includes a conductive tube that the memory metal antenna 440 is inserted into, and the conductive tube is compressed to form a solid electrical and mechanical connection with the memory metal antenna 440. For another embodiment, the conductive receiving unit interface 420 include "wings" that extend out for receiving the memory metal antenna, and are the compressed around the memory metal antenna 440 to form a solid electrical and mechanical connection with the memory metal antenna 440. For an embodiment, the "wings" are formed as a result of the compression of the conductive receiving unit interface 420.

The conductive receiving unit interface 420 is electrically connected to, for example, a conductive trace 410 of the circuit board. Through conductive traces, the memory metal antenna 440 is electrically connected to electronic circuits 430 of the circuit board 400.

As described, for at least some embodiments, the memory metal antenna 440 is electrically connected to the circuit board 400 of the building control sensor unit. For embodiment, the building control sensor unit is enclosed within a metallic enclosure, and the extended antenna extends out of the metallic enclosure and into the structure. As described, for an embodiment the extended antenna is functional to deform from an operational position during shipping of the building control sensor unit, and spring back to the operational position when deployed for operation. For at least some embodiments, the memory metal of the extended antenna includes a Nickel Titanium alloy also known as Nitinol or NiTi. For at least some embodiments, the extended antenna includes a single strand of memory metal. For at least some embodiments, the extended antenna includes multiple strands, and other memory metal antenna configurations. For at least some embodiments, the strand of memory metal comprises a diameter of approximately 0.1 Millimeter. For an embodiment, the memory metal comprises a diameter of approximately 0.1 Millimeter, plus or minus approximately 0.05 Millimeters.

Figure 5:
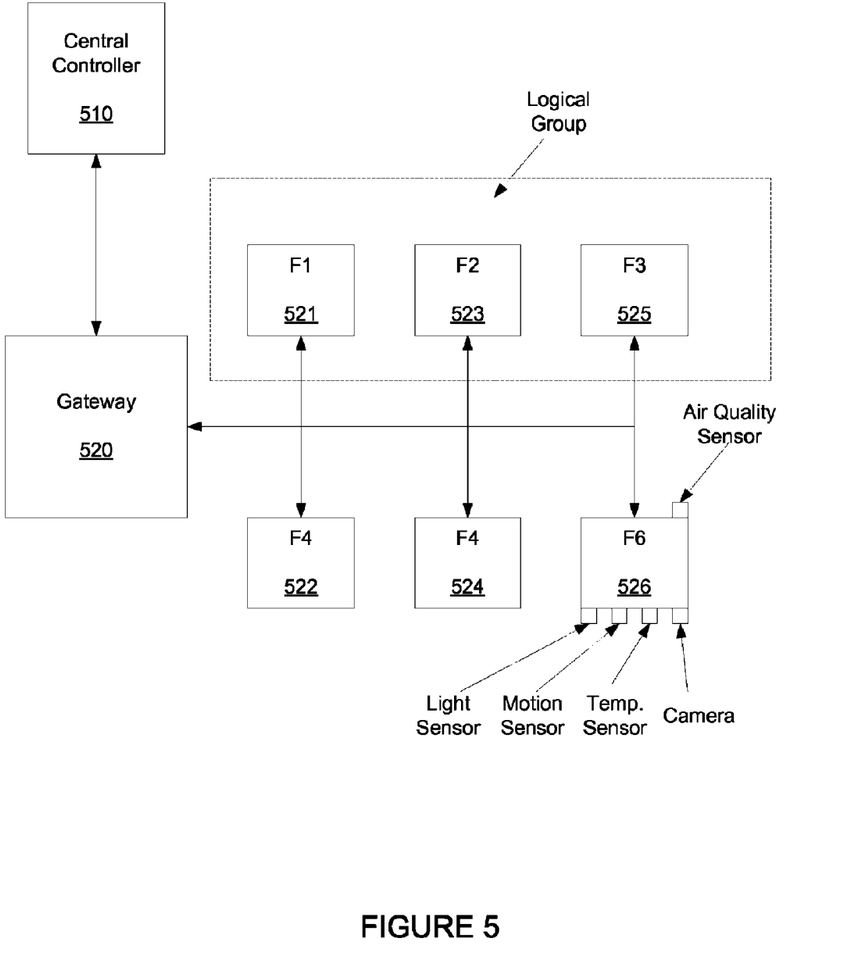
FIG. 5 shows a plurality of independently controllable light fixtures that are members of a group, according to an embodiment.

FIG. 5 shows an example of a plurality of independently controlled light fixtures 521, 522, 523, 524, 525, 526 that are interfaced with a central controller 510. For this embodiment, a gateway 520 is included within a communications path (second communication link) between the central controller 510 and the plurality of fixtures 522, 523, 524, 525, 526. The central controller 510 can initially provide each of the plurality of fixtures 522, 523, 524, 525, 526 with a light profile.

As shown, the independently controlled lights can include any number of sensors. The sensors can include, for example, a light sensor, a motion sensor, a temperature sensor, a camera, and/or an air quality sensor. Information obtained from the sensors can be used directly by the independently controlled light itself, or at least some of the information can be fed back to the central controller 510, through, for example, a gateway 520.

As shown, a plurality of the fixtures (such as, fixtures 521, 523, 525) can be included within a logical group. A user device can establish a direct communication link with any one of the fixtures. If the fixture is within a logical group, the user device can then control fixtures within the logical group by sending control information to the central controller 510. The controller can then control the fixtures of the logical group through communications through the communications link.

Various embodiments include logical groups of fixtures that map onto, for example, a large conference room or a presentation hall. A user's direct communication link with any one of the fixtures within the conference room or presentation hall provides the user with access to a logical switch capable of controlling the entire space with preset scenes etc. That is, by accessing the logical switch through a direct link to any one of the fixtures of the logical group, the user can control the logical group. For an embodiment, the logical switch is configured by software operating on the fixtures (CPU of the high-voltage manager and/or CPU of the building control sensor unit) and/or the central controller. The control of the logical switch offered to the user includes selection of an intensity of light of the logical group, and/or the selection of predetermined scenes associated with the logical group. For an embodiment, the logical groups are automatically determined by each of the fixtures (that is, building control sensor units of the fixtures) sensing other proximate fixtures. This can be accomplished, for example, by proximate fixtures sensing motion or light intensity changes simultaneously. That is, due to their proximity, they sense changes near-simultaneously.

Although specific embodiments have been described and illustrated, the described embodiments are not to be limited to the specific forms or arrangements of parts so described and illustrated. The embodiments are limited only by the appended claims.

What is claimed:

1. A building control sensor unit, comprising:
   one or more sensors operative to sense an environmental condition of a structure;
   a transceiver, wherein the transceiver includes an extended antenna, wherein the extended antenna includes a strand of memory metal, wherein the strand of memory metal is configured to maintain an extended shape even when temporarily deformed;

a controller, wherein the controller is operative to receive information from other building control sensor units or a central controller, and transmit information to the other building control sensor units or the central controller;

wherein the building control sensor unit is configured whereby when placed on or within a ceiling of the structure, the extended antenna extends into the structure.

2. The building control sensor unit of claim 1, wherein the building control sensor unit comprises a circuit board that provides an electrical interface between the extended antenna and the controller.

3. The building control sensor unit of claim 2, wherein the electrical interface comprises a conductive receiving unit, wherein the extended antenna extends into the conductive receiving unit.

4. The building control sensor unit of claim 3, wherein the extendable antenna maintains electrical contact with the conductive receiving unit due to the conductive receiving unit being deformed around at least a portion of the extendable antenna, and wherein the extendable antenna is a fixed position due to the conductive receiving unit being deformed around the at least the portion of the extendable antenna.

5. The building control sensor unit of claim 1, wherein the building control sensor unit is enclosed within a metallic enclosure, and the extended antenna extends out of the metallic enclosure and into the structure.

6. The building control sensor unit of claim 1, wherein the extended antenna is functional to deform from an operational position during shipping of the building control sensor unit, and spring back to the operational position when deployed for operation.

7. The building control sensor unit of claim 1, wherein the memory metal of the extended antenna includes a Nickel Titanium alloy.

8. The building control sensor unit of claim 1, wherein the extended antenna includes a single strand of memory metal.

9. The building control sensor unit of claim 1, wherein the extended antenna includes multiple strands, and other memory metal antenna configurations.

10. A building control system comprising:
a plurality of building control sensor units, wherein at least one of the plurality of building control sensor units communicates with at least one of another one of the plurality of building control sensor units or a central control unit; and
wherein the at least one of the plurality of building control sensor units comprises:
one or more sensors operative to sense an environmental condition of a structure;
a transceiver, wherein the transceiver includes an extended antenna, wherein the extended antenna includes a strand of memory metal, wherein the strand of memory metal is configured to maintain an extended shape even when temporarily deformed;
a controller, wherein the controller is operative to receive information from other building control sensor units or the central controller, and transmit information to the other building control sensor units or the central controller;
wherein the at least one of the plurality of building control sensor units is configured whereby when placed on or within a ceiling of the structure, the extended antenna extends into the structure.

11. The building control system of claim 10, wherein the at least one of the plurality of building control sensor units comprises a circuit board that provides an electrical interface between the extended antenna and the controller.

12. The building control system of claim 11, wherein the electrical interface comprises a conductive receiving unit, wherein the extended antenna extends into the conductive receiving unit.

13. The building control system of claim of claim 12, wherein the extendable antenna maintains electrical contact with the conductive receiving unit due to the conductive receiving unit being deformed around at least a portion of the extendable antenna, and wherein the extendable antenna is a fixed position due to the conductive receiving unit being deformed around the at least the portion of the extendable antenna.

14. The building control system of claim 10, wherein the at least one of the plurality of building control sensor units is enclosed within a metallic enclosure, and the extended antenna extends out of the metallic enclosure and into the structure.

15. The building control system of claim 10, wherein the extended antenna is functional to deform from an operational position during shipping of the building control sensor unit, and spring back to the operational position when deployed for operation.

16. The building control system of claim 10, wherein the memory metal of the extended antenna includes a Nickel Titanium alloy.

17. The building control system of claim 10, wherein the extended antenna includes a single strand of memory metal.

18. The building control system of claim 10, wherein the extended antenna includes multiple strands, and other memory metal antenna configurations.

19. The building control system of claim 10, further comprising a high-voltage manager, wherein the high-voltage manager receives a high-voltage power and steps down the high-voltage power to a low-voltage power, and provides the low-voltage power to each of the plurality of building control sensor units.

20. The building control system of claim 19, further comprising a processing unit of the high-voltage manager communicating with an external controller through at least one of the plurality of building control sensor units.

* * * * *